US008077309B2

(12) United States Patent
Brown et al.

(10) Patent No.: US 8,077,309 B2
(45) Date of Patent: Dec. 13, 2011

(54) CHEMICAL ANALYZER FOR INDUSTRIAL PROCESS CONTROL

(75) Inventors: Gordon C. Brown, Walpole, NH (US); Michael Burka, Winchester, MA (US); Brian Cranton, Sanbornton, NH (US); David Erickson, Topsfield, MA (US); James Grassi, Westwood, MA (US); Matthew Patrick Hammond, Boston, MA (US); Maximillan Ben Shaffer, Boston, MA (US); Pierre Villeneuve, Winchester, MA (US)

(73) Assignee: Applied Instrument Technologies, Inc., Upland, CA (US)

( * ) Notice: Subject to any disclaimer, the term of this patent is extended or adjusted under 35 U.S.C. 154(b) by 0 days.

(21) Appl. No.: 11/668,083

(22) Filed: Jan. 29, 2007

(65) Prior Publication Data

US 2008/0180661 A1    Jul. 31, 2008

(51) Int. Cl.
*G01J 3/44* (2006.01)

(52) U.S. Cl. .................................................. 356/301

(58) Field of Classification Search .................. 356/301, 356/303, 305, 317, 318, 320, 323, 326, 328, 356/73
See application file for complete search history.

(56) References Cited

U.S. PATENT DOCUMENTS

| | | | |
|---|---|---|---|
| 4,648,714 A | 3/1987 | Benner et al. | |
| 4,784,486 A * | 11/1988 | Van Wagenen et al. | 356/301 |
| 4,986,655 A | 1/1991 | Sweeney et al. | |
| 5,357,343 A | 10/1994 | Lowne et al. | |
| 5,386,295 A | 1/1995 | Switalski et al. | |
| 5,521,703 A | 5/1996 | Mitchell | |
| 5,526,121 A | 6/1996 | Sandifer et al. | |
| 5,754,289 A | 5/1998 | Ozaki et al. | |
| 5,864,397 A * | 1/1999 | Vo-Dinh | 356/301 |
| 5,963,319 A * | 10/1999 | Jarvis et al. | 356/301 |
| 6,244,753 B1 | 6/2001 | O'Connor et al. | |
| 6,373,567 B1 | 4/2002 | Wise et al. | |
| 7,256,916 B2 * | 8/2007 | Lee et al. | 359/196 |
| 7,295,309 B1 * | 11/2007 | Morrison | 356/335 |
| 7,359,040 B1 * | 4/2008 | Pendell-Jones et al. | 356/73 |
| 2004/0169854 A1 * | 9/2004 | Vo-Dinh et al. | 356/301 |
| 2005/0046850 A1 * | 3/2005 | Chow | 356/430 |
| 2005/0248758 A1 | 11/2005 | Carron et al. | |

(Continued)

FOREIGN PATENT DOCUMENTS

| | | |
|---|---|---|
| CN | 1049227 | 2/1991 |
| CN | 1183576 | 6/1998 |
| JP | 60053834 | 3/1985 |
| WO | 9822850 | 5/1998 |

OTHER PUBLICATIONS

International Search Report issued in connection with International Application No. PCT/US2008/051259 mailed on Aug. 21, 2008.

(Continued)

*Primary Examiner* — Tarifur Chowdhury
*Assistant Examiner* — Abdullahi Nur
(74) *Attorney, Agent, or Firm* — Gesmer Updegrove LLP (57) ABSTRACT

An optical apparatus for measurement of industrial chemical processes. The analyzer uses Raman scattering and performs measurement of chemical concentrations in continuous or batch processes. The analyzer operates at a standoff distance from the analyte (or analytes) and can measure concentrations through an optical port, facilitating continuous, non-destructive, and non-invasive analysis without extracting the analyte or analytes from the process. The analyzer can measure one or several solid, liquid, or gaseous analytes, or a mixture thereof.

29 Claims, 4 Drawing Sheets

U.S. PATENT DOCUMENTS

| | | | |
|---|---|---|---|
| 2006/0103840 A1* | 5/2006 | Fritz et al. | 356/301 |
| 2006/0170917 A1 | 8/2006 | Vakhshoori et al. | |
| 2007/0030488 A1* | 2/2007 | Harrison | 356/445 |
| 2007/0216898 A1* | 9/2007 | Gardner | 356/301 |

OTHER PUBLICATIONS

International Preliminary Report on Patentability issued in connection with International Application No. PCT/US2008/051259 mailed on Mar. 26, 2009.

European Office Action issued on Nov. 11, 2009 in connection with corresponding European Application No. 08705972.1.

Written Opinion issued in connection with the International Application No. PCT/US2008/051259 mailed on Aug. 21, 2008.

Chinese Office Action issued in connection with corresponsing Chinese Application No. 20088003475.9, issued Jan. 19, 2011, and English translation thereof.

English translation of the Chinese Office Action issued in connection with corresponding Chinese Application No. 20088003475.9, issued Jun. 28, 2010.

* cited by examiner

CHEMICAL ANALYZER FOR INDUSTRIAL PROCESS CONTROL

BACKGROUND OF THE INVENTION

Defined as the analysis of material properties in industrial manufacturing processes, process analysis has been performed for several decades in a wide variety of industries. These industries include chemical, petrochemical, petroleum, pharmaceutical, food & beverage, pulp & paper, and agricultural. A former common implementation of process analysis consisted of manually extracting samples from a process and carrying the samples to a laboratory for analysis. Over time, process analysis evolved from off-line analysis to a continuous on-line analysis where samples are extracted by automated sampling systems and carried in slip streams to process analyzers.

The primary advantage of on-line process analysis is the reduction of the time interval between sample extraction and data generation. The faster response time provides greater control of manufacturing processes leading to increased product yield, improved product quality (consistency), reduced in-process inventory, reduced operating and maintenance workforce, reduced energy consumption, reduced consumption of raw material inputs, and reduced production of waste streams.

Several instruments are currently used for industrial process monitoring. Gas chromatographs (GCs), for example, measure differences in molecular mobility to identify multi-component samples. GCs have high specificity and high sensitivity. They require shielded enclosures for protection from the environment, a supply of column gas, frequent maintenance, and water trapping especially in corrosive applications. These instruments are widely discussed in published literature.

Infrared (IR) instruments rely on material absorption to analyze samples. IR instruments include Fourier Transform Infrared (FTIR) analyzers, IR dispersive analyzers, and non-dispersive IR (NDIR) analyzers. Non-dispersive instruments include filter and non-filter based instruments. IR instruments have displaced other types of instruments due to higher speed, sensitivity, and specificity. IR instruments typically induce a net change in dipole moment in the molecules of a sample as a result of rotational or vibrational motion. The method works well for many species, but fails for homonuclear species such as nitrogen, oxygen, chlorine, hydrogen, and fluorine that cannot have a net change in dipole moment.

Electrochemical sensors provide other means for quantifying species concentrations. These types of sensors are typically limited to the measurement of a single species and often supplement IR methods.

An alternative approach for industrial process monitoring includes the use of Raman methods. Raman spectroscopy is based on the inelastic scattering of light off molecules. As a process analysis technique, Raman spectroscopy has advantages over other techniques as it requires no sample extraction or sample preparation, can perform continuous in-situ quantitative measurements, can analyze pipe content through a sight window, can detect molecules that other techniques cannot, and is unaffected by water molecules.

As a result, Raman spectrometers have found a niche in the market where no other viable solutions exist. Despite these advantages, broad adoption of Raman spectrometers has been hindered because they are very expensive to buy, install and maintain, require frequent calibrations and skilled operators and, in general, lack the robustness necessary to operate in harsh plant environments.

In order for a Raman instrument to be widely accepted for industrial process monitoring, it must have low cost and have high performance. The present invention uses fewer and more readily available components than other Raman instruments, and is easily manufactured and adapted to different applications. It eliminates the use of optical fiber hence achieves high optical throughput. The invention also uses increased amplification with robust multi-stage photon-to-electron amplifiers, and optimized optical filter designs. Further, the invention can withstand tough industrial conditions and uses low cost and wavelength stabilized laser sources.

Raman spectrometers are part of a general class of instruments called optical analyzers. Optical analyzers are generally based on one of six phenomena: absorption, fluorescence, phosphorescence, scattering, emission, and chemoluminescence. These phenomena can occur in the ultraviolet, visible, and infrared portions of the spectrum. A typical instrument contains five basic elements: a radiation source, a sample container, a spectral element to look at a specific region of the spectrum, a detector that converts photons to electrons, and a signal processor. Raman is classified as a second order scattering process in that Raman scattered photons are created from the inelastic interaction of incident light photons with the molecules of the sample. These second order photons are weak, typically $10^6$ to $10^7$ times less intense than first order elastically-scattered photons.

U.S. Pat. Nos. 4,648,714, 4,784,486, 5,521,703, and 5,754,289 use Raman scattering to perform gas analysis. Gases flow through a section of tube while a laser beam is directed into it. These inventions require a slip stream or redirection of the sample away from a pipeline or reactor. Most use a filter wheel in conjunction with a single detector. U.S. Pat. No. 5,521,703 differs slightly from the other three in that its multiple detectors are arranged along the length of gas sampling cell within a laser resonator configuration. U.S. Pat. No. 5,754,289 teaches the use of a filter wheel in conjunction with an integrating sphere for the sample. The related U.S. Pat. Nos. 5,386,295, 5,357,343, and 5,526,121 teach the use of a filter wheel spectrometer coupled to reference and sample elements using fiber optic probes. U.S. Pat. Nos. 5,963,319 and 6,244,753 teach the use of a dispersive spectrometer and fiber optic couplers for industrial process monitoring. Fiber optic couplers are known to limit optical throughput.

SUMMARY OF THE INVENTION

The present invention provides a photometric analyzer incorporated into a small, low cost, and robust package for in-situ industrial process monitoring applications. The analyzer can measure homogeneous or inhomogeneous chemical mixtures made up of one or several solid, liquid, or gaseous analytes. The analyzer uses Raman scattering and maximizes optical throughput, increases the signal-to-noise ratio of the system, and incorporates on-board quantification of process concentrations. The present invention requires neither extraction nor redirection of material from the originating process pipeline or vessel. It can analyze chemical concentrations remotely from a process, i.e. the analyzer can be separated or physically detached from the process pipeline or vessel. The present invention can analyze chemical composition in processes operating under a wide range of conditions. Examples include process pressures from sub-atmospheric to thousands of psi, process temperatures from sub-zero to hundreds of degrees Celsius, and process flows from stagnant to hundreds of liters per minute.

The analyzer comprises a laser radiation source, which may be any type of laser but preferably a solid state laser diode. The temporal characteristics of the laser radiation are controlled by an integrated laser controller module that, in turn, is controlled by a microprocessor. The laser output is spatially shaped and directed across a free-space light path toward the process sample. Free-space propagation is defined as the propagation of an optical beam predominantly through gases or vacuum with discrete optical components and windows to control focus, spectral characteristics, and other properties. The laser radiation is then incident upon the sample located outside the analyzer. The Raman radiation scattered by the sample is collected by the free-space shaping optics of the analyzer, which adjust the spatial characteristics of the scattered radiation for transport to the detector module. One or more spatial and/or optical filters are used to reduce or eliminate the amount of radiation at the excitation wavelength that is introduced into the detector module without substantially reducing the amount of desired Raman signal. One or more additional filters are used to extract targeted spectral bands from the Raman signal. The signal of each spectral band passes through low-noise, high-gain amplifiers that increase analog signal levels without introducing significant perturbations. The analog signal levels are quantitatively measured by means of analog-to-digital signal converters. The resulting digital signals are processed by a dedicated embedded microprocessor or some other data control system. Using calibration information from known sources such as chemical samples or suitable reference standards, the signals generate a quantitative measurement of the analytes either directly or via a mathematical deconvolution.

The present invention can be customized for specific applications by identifying which of several chemical species are to be measured. Ideally, the Raman radiation of the desired chemical species comprises spectral components that are largely independent from the scattered radiation of the other molecules.

DETAILED DESCRIPTION OF THE INVENTION

Figure 1:
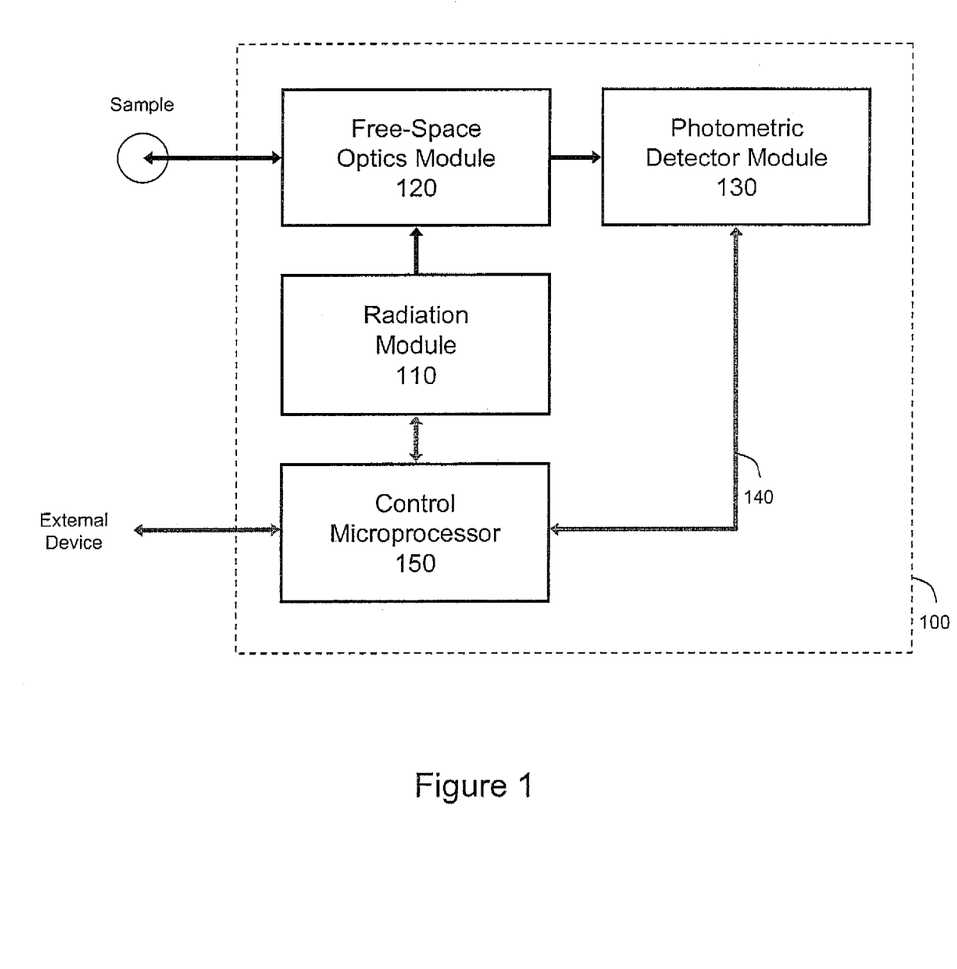
FIG. 1 is a schematic representation of the invention.

A schematic representation of the invention is shown in FIG. 1. The black arrows indicate the direction of the primary optical signals; the gray arrows indicate the direction of the primary electrical signals. A radiation module 110 which includes a laser radiation source is controlled by a control microprocessor 150. The laser source can be of any type but is preferably a solid state laser diode. In a preferred embodiment of the invention, the laser radiation source emits radiation primarily at a wavelength of 785 nm.

After leaving the radiation module, the laser radiation is transferred via free-space optics to a free-space optics module 120. In a preferred embodiment of the invention, the optics module includes a selective reflector which treats the laser radiation differently than other radiation, in particular the radiation that comprises the return signal (defined below). The selective reflector may reflect the laser radiation while allowing other radiation to pass through, or may allow the laser radiation to pass through while reflecting other radiation. The selective reflector relies on one, or a combination of several, mechanisms including: (i) spatial selectivity such as the deposition of a mirror or transparent aperture in one portion of the selective reflector; (ii) wavelength selectivity; or (iii) polarization selectivity. In one preferred embodiment, the selective reflector has a large clear area with a small reflective spot in its center to reflect the collimated laser radiation. In another preferred embodiment, the selective reflector comprises a dichroic filter or is coated with an optical thin film that reflects light at the excitation laser wavelength and transmits light at longer and shorter wavelengths.

After leaving the optics module 120, the laser radiation exits the analyzer 100 and is incident upon a sample located outside the analyzer. The sample may be any of a large number of chemical materials and may or may not be contained behind a sample port window that is transparent to both the laser radiation and the return-signal radiation. The sample and sample port window are not part of the analyzer. The analyzer relies on Raman scattering of laser radiation by the sample. The physical processes that govern this scattering generally include both inelastic scattering (wavelength-shifting) processes, such as Raman scattering, and elastic scattering (wavelength-preserving) processes such as Rayleigh and Mie scattering. The desired signal (known as the return signal) includes the inelastically scattered Raman radiation; the undesired signal (known as the noise) includes elastically scattered radiation plus parasitical sources such as stray light. A portion of the return signal and noise is collected by the free-space optics module 120 and makes up the return radiation (known as the backscattered radiation). The spatial and spectral characteristics of the return radiation are adjusted by the free-space optics module. One or more spatial and/or optical filters are used to reduce or eliminate the amount of radiation at the excitation wavelength without substantially reducing the amount of desired return signal. After exiting the optics module, the return radiation is transferred via free-space optics to the photometric detector module 130.

The photometric detection module includes one or more filters that extract targeted spectral bands from the return signal corresponding to specific chemicals of interest. The filters can be bandpass or notch filters, and can be fixed-wavelength or tunable filters. After separation from the composite beam, the selected wavelengths of light are directed to photo-sensitive detectors capable of detecting photon streams. The detectors generate analog voltage and/or current responses which are proportional to the number of photons detected at a given time. The composite signal-bearing light-stream is divided into discrete paths such that the photo-detectors receive measurable quantities of light in real time. In a preferred embodiment of the invention, multiple filters and multiple detectors are used to measure multiple wavelength components simultaneously. An advantage of simultaneous detection is the reduction of the total signal collection time to achieve a desired measurement sensitivity. Another advantage of simultaneous detection is the ability to distinguish analyte concentration changes from common mode effects such as sample density changes or variations in sample transparency to incident radiation. In another preferred embodiment of the invention, the filters are positioned on a movable stage such as a rotating wheel, linear slide, or other geometric configuration permitting wavelength separation. In a third preferred embodiment of the invention, wavelengths are separated using an electro-optic filter utilizing either Pockels or Kerr media for the monochromator. An advantage of using a tunable filter, electro-optic filter, or movable stage is the ability to use a lower number of detectors. In a fourth preferred embodiment, wavelengths are separated using a diffractive element (such as a reflective or refractive grating) or a dispersive element. In this embodiment, the different wavelength components can be detected with an array of detectors.

In some cases, such as the analysis of low-pressure gas, the detector signals are increased using low-noise, high-gain amplifiers capable of increasing analog signal levels without introducing significant perturbations. In a preferred embodiment, the analog signal paths are divided into stages, each designed for stability and low susceptibility to electronic and thermal noise. The inputs to each amplifier are shielded to prevent electronic pickup of signal from external sources. The analog signal levels are quantitatively measured by means of analog-to-digital signal converters.

Two-way communication between the photometric detection module and control microprocessor 150 is carried on digital control bus 140. In a preferred embodiment of the invention, each signal is monitored with a dedicated analog-to-digital converter so as to minimize integration time and add speed to the data analysis without signal degradation. The microprocessor provides digital data such as measurement data and analyzer status information to one or more external devices. In a preferred embodiment of the invention, the analyzer also employs in-situ physical presentation of data which can be monitored without an external device.

Figure 2:
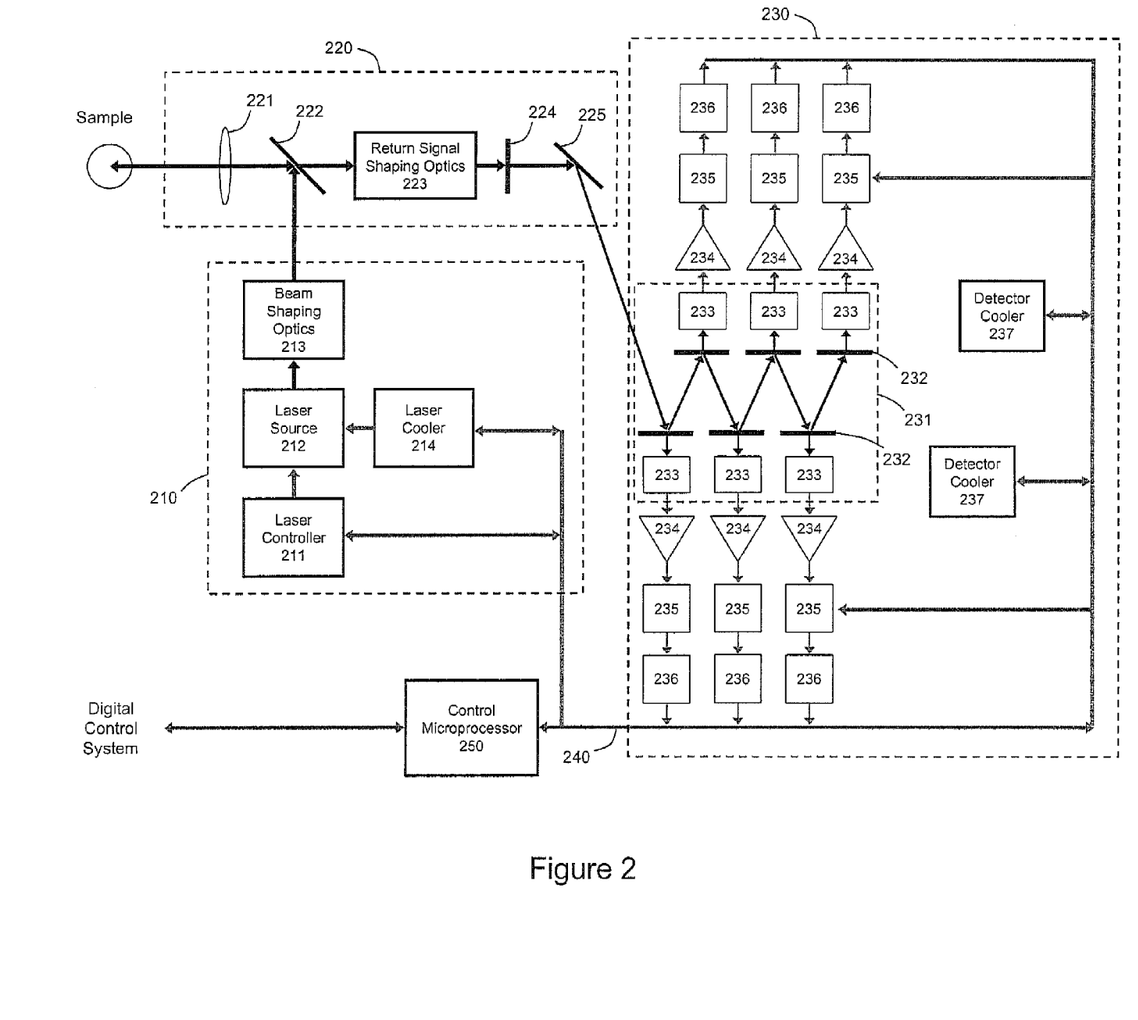
FIG. 2 is a schematic representation of a preferred embodiment of the invention.

A schematic representation of another preferred embodiment of the invention is shown in FIG. 2. Optical radiation is generated by laser source 212. The radiation source is temperature controlled by laser cooler 214, and the radiation is shaped spatially and spectrally by beam shaping optics 213, which in one preferred embodiment, include lenses to control the spatial extent and collimation of the beam, a wavelength selective reflecting element to control and stabilize the central wavelength of the beam, and optical filters to limit the spectral extent of the beam. The temporal characteristic of the laser radiation is controlled by laser controller 211 which, in turn, is controlled by control microprocessor 250. In one preferred embodiment, the temporal characteristic of the beam incorporates a boxcar modulation at a frequency below 10 MHz to facilitate discrimination against stray optical background. The laser source 212, laser cooler 214, beam shaping optics 213, and laser controller 211 are included in radiation module 210.

Upon leaving the radiation module, the laser radiation enters the free-space optics module 220. The free-space optics module includes a selective reflector 222 with a large clear area and a small reflective area in its center to reflect the laser radiation. After being reflected by the selective reflector, the laser radiation is incident upon objective lens 221 whose function it is to facilitate delivery of the laser radiation to the sample under test.

The objective lens 221 collects the backscattered radiation from the sample under test. The backscattered radiation travels to the selective reflector 222 which lets a large portion of the signal through and reflects the light in the center of the reflector. The spatial characteristics of the transmitted signal from the selective reflector are adjusted by the return signal shaping optics 223. The excitation blocking filter 224 comprises one or more lenses and one or more spatial or optical filters that serve to reduce or eliminate the amount of undesired radiation that enters the detector module 230 at the excitation laser wavelength. The excitation blocking filter 224 does not substantially reduce the amount of desired return signal but reduces the undesired elastic component of the return radiation at the excitation laser wavelength. The remaining portion of the undesired radiation is monitored to serve as a diagnostic signal that contains information regarding the operation of the instrument and the condition of the process being analyzed.

The signal leaving the excitation blocking filter is incident upon one or more mirrors 225 that serve to redirect the signal towards the photometric detector module 230 and facilitate optical alignment of the analyzer. The detector module includes a filter module 231. Upon entering the filter module, the return signal is incident at non-normal angles upon a multiplicity of optical bandpass filters 232, each of which selectively transmits radiation at a fixed and narrow wavelength band and reflects radiation of other wavelengths towards the next filter in the chain, thus creating a devious and divaricate optical path within the filter module. Signal that is transmitted through any of the bandpass filters is focused by a detector lens onto a photodetector element 233. Examples of photodetector elements include Silicon photodetectors, avalanche photodetectors, or photomultiplier tubes. Although six filters and detector elements are shown in FIG. 2, the analyzer is operable with any number of filters and detector elements. In an alternate embodiment of the invention, the filters are positioned on a movable stage such as a rotating wheel or a linear slide.

In a preferred embodiment of the invention, the optical bandpass filters 232 are assembled in removable and replaceable cartridges. These cartridges are designed such that the filters 232 are pressed and held against a reference surface to provide a low-cost, easily-reconfigurable, and easily-manufacturable assembly. In the specific embodiment shown in FIG. 2, two cartridges can be used each holding half the filters.

The output currents from the photodetector elements 233 are amplified and converted to signal voltages by photodetector amplifiers 234. Since the laser source 212 is modulated, the photons scattered by the sample have a distinct identification and are differentiated from undesired photons from other sources. The signals from the photodetector amplifiers 234 are demodulated into DC voltage or electronic current signal levels by lock-in amplifiers 235. Each demodulator is synchronously tied to the laser excitation modulation to allow for in-phase measurements.

The analog signal levels are quantitatively measured by means of analog-to-digital signal converters 236. In a preferred embodiment of the invention, these signal converters perform high-resolution averaging functions. Unwanted noise (including noise generated by the modulation source) is filtered, which provides more accurate DC measurements.

The photodetector elements 233 are actively temperature stabilized by heating and/or cooling devices 237 coupled with a PID loop temperature controller in order to minimize thermal noise and drift.

The analyzer is calibrated after assembly using known quantities of reference chemicals or a calibrated fluorescence source. The intensity of the optical signal is directly proportional to the molecular density. This proportionality provides a way to relate observed Raman photon power to sample composition. Alternatively, a quantitative measurement of the chemicals can be generated using a mathematical deconvolution employing information from a combination of photodetector elements. In another embodiment of the invention, the signals from the photodetector elements are used to provide non quantitative information about a process such as changes in concentration as a function of time or operating conditions. With the information provided by the analyzer, a user can adjust or otherwise control process conditions.

Figure 3:
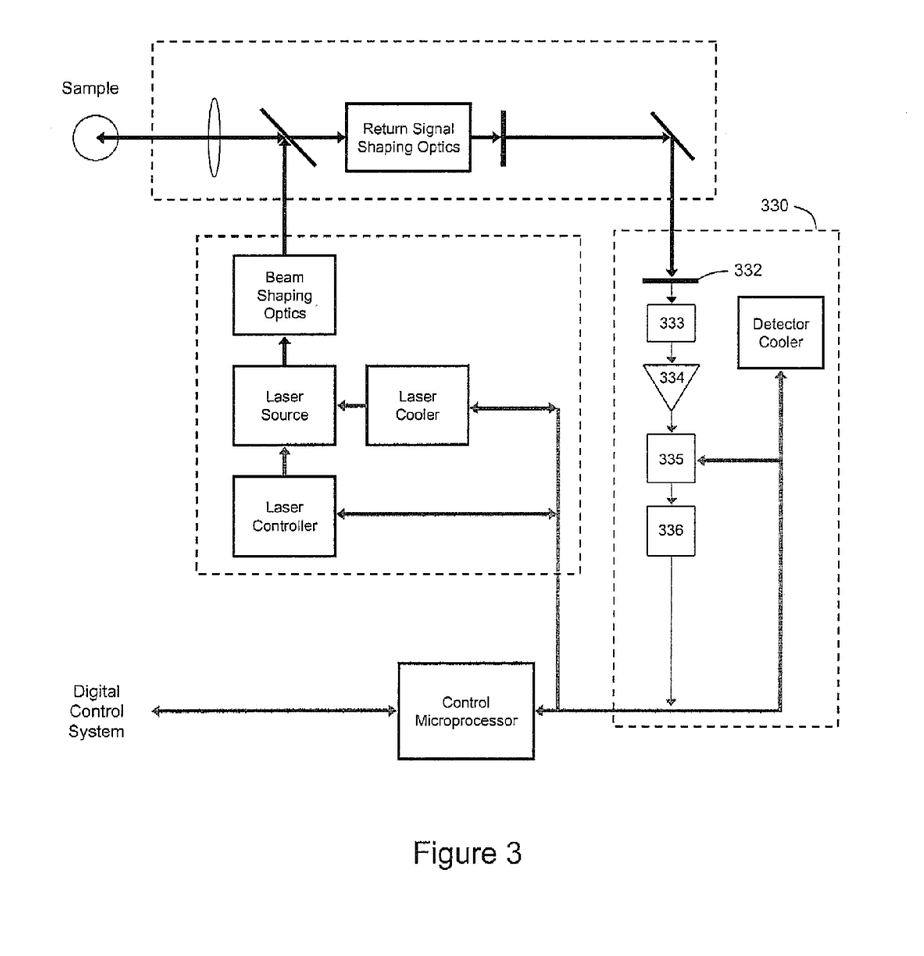
FIG. 3 is a schematic representation of another preferred embodiment of the invention.

A schematic representation of another preferred embodiment of the invention is shown in FIG. 3. This embodiment is similar to the one shown in FIG. 2 except for the detector module 330. The detector module contains a single detector element 333. The optical filtering element 332 comprises either a single variable filter (such as a tunable filter or an electro-optic filter) or multiple fixed filters on a movable stage (such as a rotating wheel or linear slide). The optical filtering element 332 selectively transmits radiation at a desired wavelength band. The transmitted signal is detected by detector element 333. Examples of detector elements include Silicon photodetectors, avalanche photodetectors, or photomultiplier tubes. A different wavelength band is allowed through the filtering element 332 by changing the properties of the filtering element or by moving the stage.

The output current from the detector element 333 is amplified and converted to signal voltages by a detector amplifier 334. The signal from the detector amplifier 334 is demodulated into DC voltage or electronic current signal level by a lock-in amplifier 335. The analog signal levels are quantitatively measured using a high-resolution analog-to-digital signal converter 336.

In another preferred embodiment of the invention, one or more additional filters and detectors are added to the detector module 330 in order to analyze other desired wavelength bands.

Figure 4:
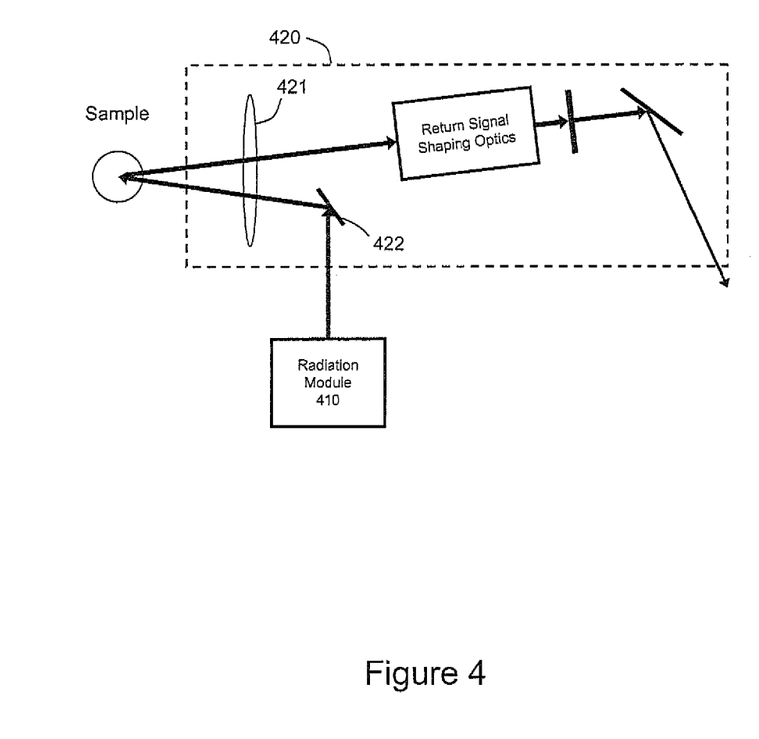
FIG. 4 is a schematic representation of a portion of the optical layout of yet another preferred embodiment of the invention.

A schematic representation of a portion of yet another preferred embodiment of the invention is shown in FIG. 4. Laser radiation from radiation module 410 is incident on free-space optics module 420. The objective lens 421 is common to both the laser radiation delivery and return signal collection but, unlike in the specific embodiment presented in FIG. 2, the selective reflector 422 is used only to deliver the laser radiation to the sample. In the specific embodiment shown in FIG. 4, selective reflector 422 need not be wavelength selective.

Although the invention has been shown and described with respect to several exemplary embodiments thereof, various changes, omissions and additions to the form and detail thereof, may be made therein, without departing from the spirit and scope of the invention.

What is claimed is:

1. An optical chemical analyzer comprising:
a laser module including a laser source;
a free-space optics module including a filter arrangement comprising at least one excitation blocking filter to reduce or eliminate undesired radiation at the wavelength of said laser source, wherein said optics module transfers radiation of said laser source through an optical window or lens to a sample located outside said analyzer and at a standoff from said analyzer, said optics module collects scattered Raman radiation from said sample through said optical window or lens and transfers said collected Raman radiation to a photometric detector module, said photometric module including a second filter arrangement comprising at least one fixed-wavelength extraction filter and at least one photodetector, each of said extraction filter extracts one or more spectral bands from said collected Raman radiation so as to generate quantitative measurement of analyte concentration; and
a control microprocessor.

2. The optical chemical analyzer of claim 1, wherein said extraction filters are bandpass filters or notch filters.

3. The optical chemical analyzer of claim 2, wherein said extraction filters are positioned on a devious and divaricate optical path.

4. The optical chemical analyzer of claim 3, wherein said Raman radiation is incident on said extraction filters at non-normal angles.

5. The optical chemical analyzer of claim 2, wherein said extraction filters are thin-film filters.

6. The optical chemical analyzer of claim 1, wherein said optical detector module further includes at least one tunable filter.

7. The optical chemical analyzer of claim 1, wherein each said spectral band is detected by a different photodetector.

8. The optical chemical analyzer of claim 7, wherein each said photodetector is a Silicon photodetector, avalanche photodetector, or photomultiplier tube.

9. The optical chemical analyzer of claim 7, wherein said photodetectors are actively temperature stabilized by heating or cooling devices.

10. The optical chemical analyzer of claim 1, wherein said extraction filters are positioned on a movable stage such as a rotating wheel or linear slide.

11. The optical chemical analyzer of claim 1, wherein said extraction filters are assembled in one or more removable and replaceable cartridges, wherein said extraction filters are pressed and held against a reference surface.

12. The optical chemical analyzer of claim 1, wherein said optical detector module further includes a Pockels or Kerr medium for spectral extraction.

13. The optical chemical analyzer of claim 1, wherein said free-space optics module comprises a selective reflector which mostly reflects said laser radiation and mostly transmits said Raman radiation.

14. The optical chemical analyzer of claim 13, wherein said selective reflector comprises an optical thin film, or a dichroic filter, or a large clear area with a small reflective area located in said large clear area.

15. The optical chemical analyzer of claim 1, wherein said free-space optics module comprises a selective reflector which mostly transmits said laser radiation and mostly reflects said Raman radiation.

16. The optical chemical analyzer of claim 15, wherein said selective reflector comprises a large reflective area with a small aperture.

17. The optical chemical analyzer of claim 1, wherein principal axis of said laser radiation transferred outside of said analyzer and principal axis of said Raman radiation which enters said analyzer are collinear at the location where both said principal axes intersect said optical window or lens.

18. The optical chemical analyzer of claim 1, wherein said sample is located behind a window that is transparent to both said laser radiation and said Raman radiation.

19. The optical chemical analyzer of claim 18, wherein said sample comprises either homogeneous or inhomogeneous chemical mixtures of one or several solid, liquid, or gaseous materials.

20. The optical chemical analyzer of claim 19, wherein said sample is located inside a process pipeline or process vessel.

21. The optical chemical analyzer of claim 19, wherein said analyzer provides quantification of concentrations of at least one said solid, liquid, or gaseous material.

22. The optical chemical analyzer of claim 1, wherein amplitude of said radiation from said laser source is temporally modulated at a frequency below 10 MHz.

23. The optical chemical analyzer of claim 22, wherein said laser source is spectrally stabilized.

24. The optical chemical analyzer of claim 23, wherein said laser source emits radiation primarily at a wavelength of 785 nm.

25. The optical chemical analyzer of claim 23, wherein said laser module comprises a laser cooler, beam shaping optics, and a wavelength selective element to control the wavelength of said radiation of said laser source.

26. The optical chemical analyzer of claim 25, wherein said laser module further comprises at least one optical filter to limit the spectral extent of said radiation of said laser source.

27. The optical chemical analyzer of claim 1, wherein said optics module modifies the spatial and spectral characteristics of said collected Raman radiation, and wherein said optics module comprises at least one lens or spatial filter to reduce or eliminate undesired radiation at the wavelength of said laser source.

28. The optical chemical analyzer of claim 1, wherein at least one analog signal path in said optical detection module is divided into stages with high stability and low susceptibility to electronic and thermal noise, and wherein said control microprocessor provides digital data such as measurement data and analyzer status information to one or more external devices.

29. A method for measuring chemical concentrations in a continuous stream or batch process comprising:
  emitting laser radiation into said continuous stream or batch process through a sight window using free-space optics;
  collecting scattered Raman radiation through said sight window using an optics module;
  blocking undesired laser radiation using at least one blocking filter;
  transferring said Raman radiation to a detection module using said optics module; and
  detecting individual spectral bands of said Raman radiation using a photometric detector module comprising one or more fixed-wavelength extraction filters so as to generate quantitative measurement of analyte concentration.

* * * * *